(12) United States Patent
Kraft et al.

(10) Patent No.: US 9,768,131 B2
(45) Date of Patent: Sep. 19, 2017

(54) METHOD OF PRODUCING A SEMICONDUCTOR DEVICE WITH PROTRUDING CONTACTS

(71) Applicant: ams AG, Unterpremstaetten (AT)

(72) Inventors: Jochen Kraft, Oberaich (AT); Karl Rohracher, Graz (AT); Martin Schrems, Eggersdorf (AT)

(73) Assignee: AMS AG, Unterpremstaetten (AT)

(*) Notice: Subject to any disclaimer, the term of this patent is extended or adjusted under 35 U.S.C. 154(b) by 0 days.

(21) Appl. No.: 15/117,175

(22) PCT Filed: Jan. 14, 2015

(86) PCT No.: PCT/EP2015/050592
§ 371 (c)(1),
(2) Date: Aug. 5, 2016

(87) PCT Pub. No.: WO2015/117800
PCT Pub. Date: Aug. 13, 2015

(65) Prior Publication Data
US 2016/0351515 A1 Dec. 1, 2016

(30) Foreign Application Priority Data
Feb. 6, 2014 (EP) .................. 14154132

(51) Int. Cl.
*H01L 21/76* (2006.01)
*H01L 21/768* (2006.01)
(Continued)

(52) U.S. Cl.
CPC ............ *H01L 24/02* (2013.01); *G01N 27/12* (2013.01); *G01N 27/128* (2013.01);
(Continued)

(58) Field of Classification Search
CPC ......... H01L 24/02; H01L 21/02; H01L 21/50; H01L 21/56; H01L 21/44; H01L 21/71;
(Continued)

(56) References Cited

U.S. PATENT DOCUMENTS 5,055,426 A 10/1991 Manning
5,767,001 A 6/1998 Bertagnolli et al.
(Continued)

FOREIGN PATENT DOCUMENTS

EP 2 554 980 A1 2/2013

OTHER PUBLICATIONS

T. Helbling, et al., "Sensing NO2 with Individual Suspended Single-Walled Carbon Nanotubes," Elsevier—ScienceDirect, Sensors and Actuators B, 2008, pp. 491-497, 132.
(Continued)

*Primary Examiner* — Chuong A Luu
(74) *Attorney, Agent, or Firm* — McDermott Will & Emery LLP

(57) ABSTRACT

A wiring (3) comprising electrical conductors (4, 5, 6, 7) is formed in a dielectric layer (2) on or above a semiconductor substrate (1), an opening is formed in the dielectric layer to uncover a contact pad (8), which is formed by one of the conductors, and a further opening is formed in the dielectric layer to uncover an area of a further conductor (5), separate from the contact pad. The further opening is filled with an electrically conductive material (9), and the dielectric layer is thinned from a side opposite the substrate, so that the electrically conductive material protrudes from the dielectric layer.

5 Claims, 4 Drawing Sheets

(51) Int. Cl.
*H01L 23/00* (2006.01)
*G01N 27/12* (2006.01)
*H01L 23/48* (2006.01)

(52) U.S. Cl.
CPC ........ *H01L 21/76898* (2013.01); *H01L 24/05* (2013.01); *H01L 24/13* (2013.01); *H01L 23/481* (2013.01); *H01L 2224/02315* (2013.01); *H01L 2224/02331* (2013.01); *H01L 2224/02372* (2013.01); *H01L 2224/02373* (2013.01); *H01L 2224/0401* (2013.01); *H01L 2224/05024* (2013.01); *H01L 2224/13026* (2013.01)

(58) Field of Classification Search
CPC . H01L 21/76; H01L 21/768; H01L 21/76898; H01L 24/05; H01L 24/13; H01L 24/481
USPC .......................................................... 438/613
See application file for complete search history.

(56) References Cited

U.S. PATENT DOCUMENTS

| | | | |
|---|---|---|---|
| 5,910,020 A | 6/1999 | Yamada | |
| 6,955,937 B1 | 10/2005 | Burke et al. | |
| 7,326,465 B2 | 2/2008 | Seidel et al. | |
| 2006/0234080 A1 | 10/2006 | Seidel et al. | |
| 2006/0281296 A1* | 12/2006 | Misra | H01L 21/76898 438/618 |
| 2009/0200664 A1 | 8/2009 | Migita et al. | |
| 2013/0062755 A1 | 3/2013 | Kuo et al. | |
| 2015/0054151 A1* | 2/2015 | Choi | H01L 23/3171 257/737 |

OTHER PUBLICATIONS

S. Sonkusale, et al., "Heterogeneous Integration of Carbon Nanotubes and Graphene Microassemblies for Environmental and Breath Sensing," Design Automation Conference, 2011, pp. 723-728.

M. Wang, et al., "Interface Dynamic Behavior Between a Carbon Nanotube and Metal Electrode," Advanced Materials, Jan. 5, 2010, pp. 93-98, vol. 22, Issue 1.

* cited by examiner

METHOD OF PRODUCING A SEMICONDUCTOR DEVICE WITH PROTRUDING CONTACTS

BACKGROUND OF THE INVENTION

U.S. Pat. No. 5,767,001 discloses a semiconductor device for three-dimensional integration, which comprises contact pins penetrating a substrate and protruding from a rear surface.

U.S. Pat. No. 5,910,020 discloses a production method for semiconductor devices by forming a tungsten pillar on a wiring and applying an aluminum alloy to contact top and side surfaces of the tungsten pillar, which extend above a silicon oxide layer.

EP 2554980 A1 discloses an integrated circuit with sensor, which comprises a substrate with a stack of patterned metal layers insulated from each other by dielectric layers. An upper metal layer comprises a first electrode, a second electrode, a bond pad and a heating element.

U.S. 2009/0200664 A1 discloses a manufacturing method of semiconductor devices comprising a wafer, an SiN passivation film and a polyimide film. Metal layers include electrode pads of aluminum on the surface of the semiconductor wafer, especially a bonding pad, wiring layers, which extend above the polyimide film, and solder bumps. Some of the wiring layers are elongated in a substantially rectangular shape.

The publication of M.-S. Wang et al.: "Interface Dynamic Behavior Between a Carbon Nanotube and Metal Electrode," in Advanced Materials 22 (2010), pages 93 to 98 describes a contact between individual carbon nanotubes (CNTs) and sharpened tungsten electrodes. The tip-end of the electrode absorbs the source CNT atoms, which then penetrate deep into its body, form a carbide, and finally precipitate as freshly formed graphitic tubular shells encapsulating the electrode.

SUMMARY OF THE INVENTION

The semiconductor device comprises a semiconductor substrate, a dielectric layer on or above the substrate, a wiring comprising electrical conductors arranged in the dielectric layer, and a contact pad formed by one of the conductors. A further conductor of electrically conductive material is arranged in the dielectric layer in contact with a further one of the conductors, separate from the contact pad. The further conductor protrudes from the dielectric layer on a far side of the dielectric layer with respect to the substrate.

The semiconductor device may further comprise a passivation layer on the far side of the dielectric layer, so that the further electrical conductor also protrudes from the passivation layer. The passivation layer and the dielectric layer may comprise different materials. In particular, the dielectric layer may be a silicon oxide like $SiO_2$ and the passivation layer a silicon nitride like $Si_3N_4$, for instance.

In particular, the further conductor may have the shape of an elongate ridge with a longitudinal extension. The ridge may typically have a length along its longitudinal extension and a width transverse to its longitudinal extension, the length being at least three times the width. The further conductor may protrude by a height in the range from 20 nm to 100 nm. The further conductor may comprise a plurality of single conductors. Each of the single conductors may have the shape of an elongate ridge with a longitudinal extension, and the longitudinal extensions may especially be parallel to one another. The further conductor may comprise tungsten or copper.

A via hole may penetrate the semiconductor substrate, and a metallization may be arranged in the via hole in contact with one of the conductors, thus forming a through-substrate via.

The method comprises forming a wiring of electrical conductors in a dielectric layer on or above a semiconductor substrate, an opening in the dielectric layer to uncover a contact pad, which is formed by one of the conductors, and a further opening in the dielectric layer to uncover an area of a further one of the conductors, separate from the contact pad. The further opening is filled with an electrically conductive material, and the dielectric layer is thinned from a side opposite the substrate, so that the electrically conductive material protrudes from the dielectric layer.

In a variant of the method, the electrically conductive material is also filled in the opening uncovering the contact pad, and a portion of the electrically conductive material is removed such that a spacer is formed in the opening by a residual portion of the electrically conductive material while the further opening remains at least half filled.

In a further variant of the method, the further opening is formed by a trench.

In a further variant of the method, the further opening is formed by a plurality of parallel trenches.

In a further variant of the method, the electrically conductive material filling the further opening comprises a metal that is different from the electrical conductors.

The following is a detailed description of examples of the production method in conjunction with the appended figures.

DETAILED DESCRIPTION

Figure 1:
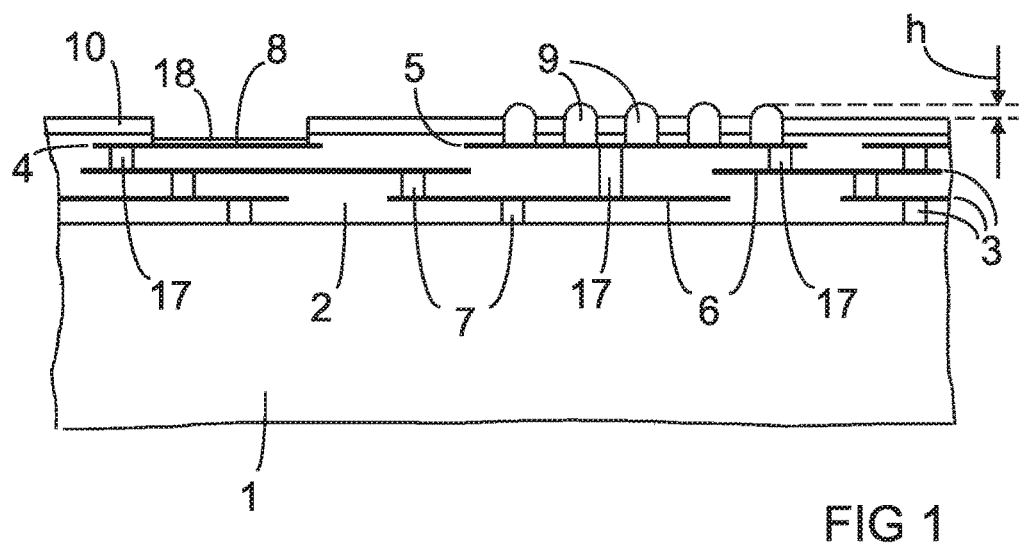
FIG. 1 is a cross section of a semiconductor device.

FIG. 1 is a cross section of a semiconductor device comprising a semiconductor substrate 1, which may be silicon, for instance, a dielectric layer 2 on the semiconductor substrate 1, and a wiring 3 embedded in the dielectric layer 2, which may be a silicon oxide, especially silicon dioxide, for instance. The wiring 3 comprises electrical conductors, which may especially be formed by structured metal layers 6 and vertical interconnections 7 like metal plugs, for instance. The wiring 3 may be provided for an integrated circuit like a CMOS circuit integrated in the semiconductor substrate 1. A contact pad 8 is formed by one of the electrical conductors 4, which may typically belong to an uppermost metallization layer.

A further one of the electrical conductors 5, which is separate from the contact pad 8, is provided with a further electrical conductor 9, which protrudes from the dielectric layer 2 on the far side with respect to the semiconductor substrate 1. A passivation layer 10, which can especially be formed from a material different from the material of the dielectric layer 2 and may comprise a silicon nitride like $Si_3N_4$, for instance, can be applied on the dielectric layer 2 as shown in FIG. 1. If a passivation layer 10 is present, the further conductor 9 also protrudes from the passivation layer 10. The height h by which the further conductor 9 protrudes may be typically in the range from 20 nm to 100 nm. The contact pad 8 may be provided in standard fashion with further electrically conductive material like an underbump metallization 18, for instance.

Figure 2:
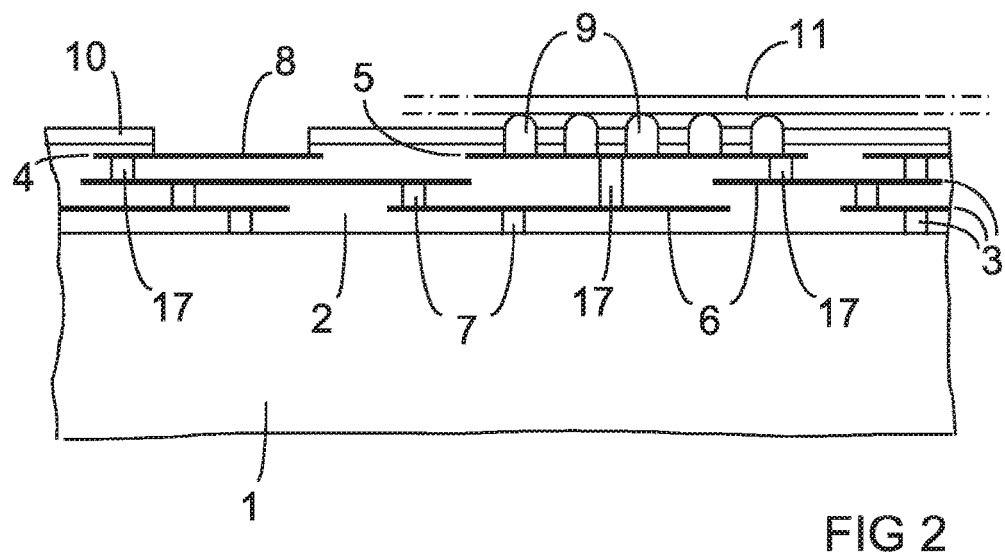
FIG. 2 is a cross section according to FIG. 1 including an arrangement of nanotubes.

FIG. 2 is a cross section according to FIG. 1 and schematically indicates an arrangement of the semiconductor device with a further device, which may especially be a gas sensor, a chemical sensor or a humidity sensor, which may be provided with a gas-sensitive material like $SnO_2$ or carbon nanotubes. FIG. 2 shows a parallel arrangement of nanotubes 11 contacting the protruding tips of the further conductor 9, by way of example.

Figure 3:
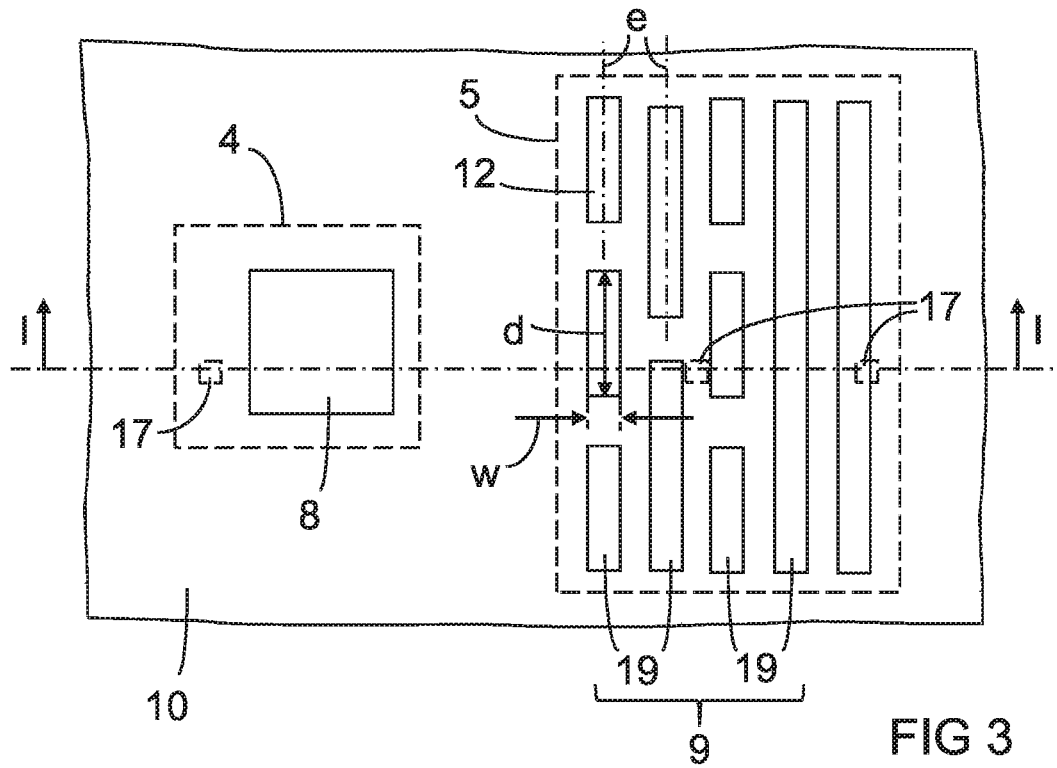
FIG. 3 is a top view of the device according to FIG. 1.

FIG. 3 is a top view of the semiconductor device according to FIG. 1. The location of the cross section shown in FIG. 1 is indicated in FIG. 3 by the horizontal dash-dotted line. Elements shown in FIG. 3 that correspond to elements shown in FIG. 1 are designated with the same reference numerals. The contact pad 8 is formed by the electrical conductor 4, which is partially covered by the dielectric layer 2 and/or the passivation layer 10. The outlines of the electrical conductor 4 and the further electrical conductor 5 are shown in FIG. 3 by broken lines as hidden contours. The positions of the vertical interconnections 17 that are connected to the electrical conductor 4 and the further electrical conductor 5 are also indicated in FIG. 3. In the semiconductor device according to FIGS. 1 and 3, the further conductor 9 comprises a plurality of single conductors 19, each of which has the shape of an elongate ridge 12 with a longitudinal extension e. The longitudinal extensions e may especially be parallel to one another. The ridges 12 may all have the same size or may instead have different sizes, as shown in FIG. 3 by way of example. The length d of a ridge 12, measured along its longitudinal extension e, exceeds its width w typically by a factor of at least three.

Figure 4:
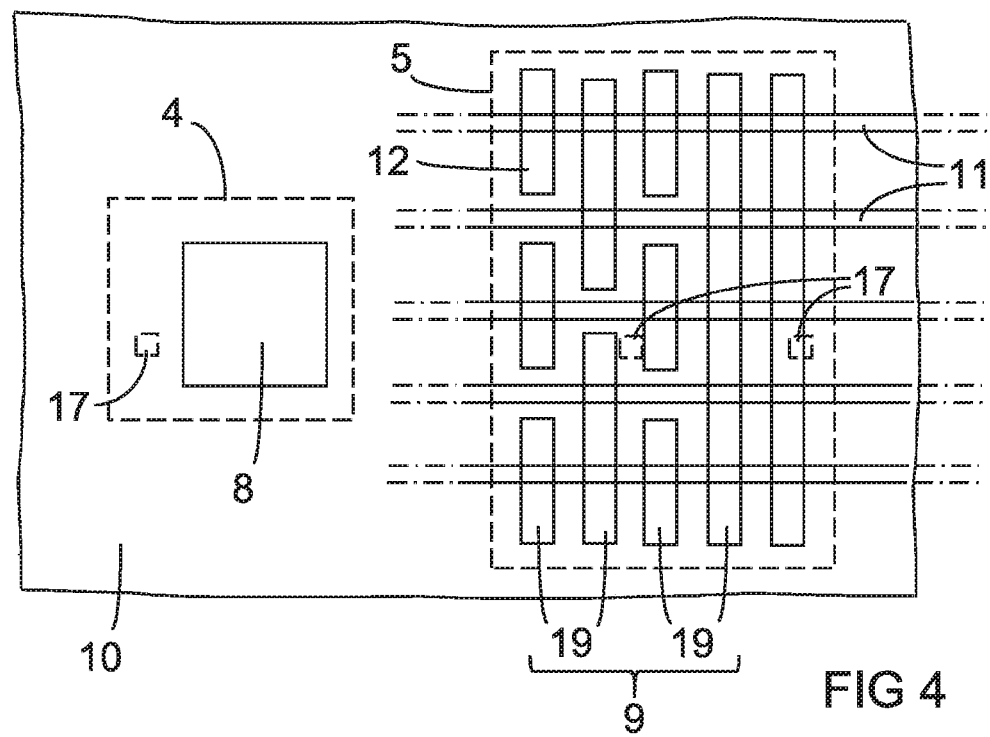
FIG. 4 is a top view of the arrangement according to FIG. 2.

FIG. 4 is a top view of the arrangement according to FIG. 2 and shows the arrangement of the nanotubes 11 extending across the single conductors 19 forming the further conductor 9. The other elements shown in FIG. 4 correspond to the elements shown in FIG. 3 and are designated with the same reference numerals. The parallel arrangement of the ridges 12 forming the single conductors 19 and the transverse parallel arrangement of the nanotubes 11 may facilitate the connection of the nanotubes 11 with the further conductor 9.

Figure 5:
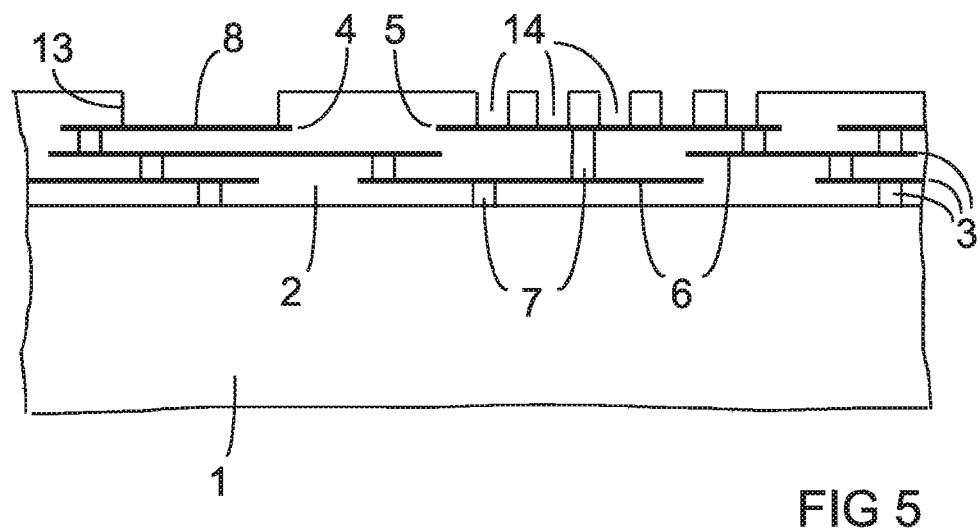
FIG. 5 is a cross section of an intermediate product of the production method.

FIG. 5 is a cross section of an intermediate product of the production method. The semiconductor substrate 1 is provided with the dielectric layer 2 including the wiring 3. FIG. 5 does not show the passivation layer 10, which can optionally be applied on the dielectric layer 2 and does not essentially change the method steps. An opening 13 is formed in the dielectric layer 2 to uncover a contact pad 8 formed by one of the conductors 4, and a further opening 14 is formed in the dielectric layer 2 to uncover an area of a further one of the conductors 5, separate from the contact pad 8. The opening 13 and the further opening 14 can be formed in the same method step, especially by using a mask with windows in the areas where the opening 13 and the further opening 14 are to be formed. In particular, the further opening 14 may be a plurality of parallel trenches, for example. The length of the trenches is larger than the width of the trenches, typically by a factor of at least three.

Figure 6:
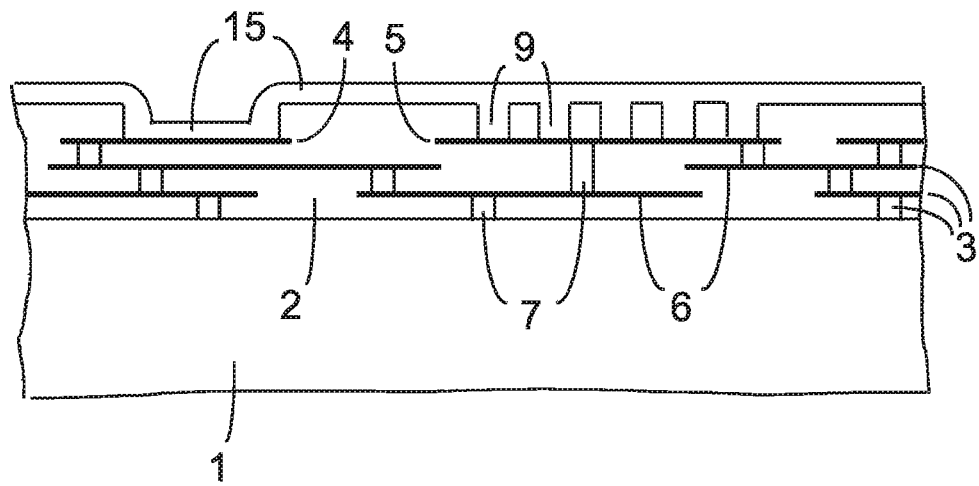
FIG. 6 is a cross section according to FIG. 5 after the application of an electrically conductive material.

FIG. 6 is a cross section according to FIG. 5 after the application of an electrically conductive material 15, especially a material comprising a metal like tungsten or copper, which may form an entire layer. Before the electrically conductive material 15 is applied, a thin liner, which may be TiN, for instance, and is not shown in FIG. 6, may be applied on the entire surface that is to be covered by the electrically conductive material 15. The further opening 14 is filled with the electrically conductive material 15, which thus forms the further conductor 9. The upper portion of the electrically conductive material 15 covering the upper surface of the dielectric layer 2 (or the passivation layer 10, if such is provided) is then removed. This may be effected by etching the electrically conductive material 15 selectively with respect to the dielectric layer 2 (or the passivation layer 10, if such is provided) and/or the liner, in particular by reactive ion etching (RIE). The etching step may produce slight depressions in the area of the further opening 14, which however remains at least half filled. The upper portion of the electrically conductive material 15 can instead be removed by chemical mechanical polishing (CMP), which yields an essentially planar surface with the further opening 14 remaining completely filled.

Figure 7:
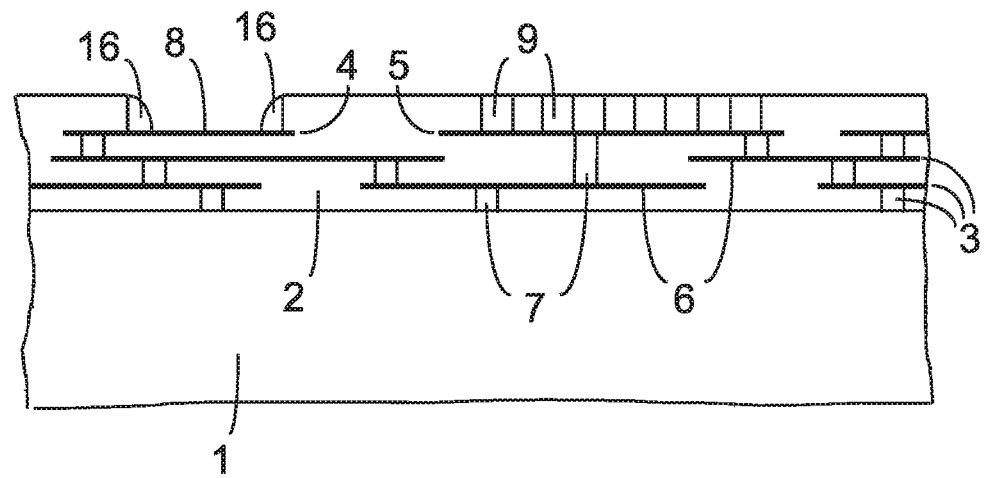
FIG. 7 is a cross section according to FIG. 6 after a partial removal of the electrically conductive material.

FIG. 7 is a cross section according to FIG. 6 after the removal of the upper portion of the electrically conductive material 15 by selectively etching. The etching step may be performed anisotropically, so that a spacer 16 consisting of a residual portion of the electrically conductive material 15 is produced at the sidewall of the opening 13 above the contact pad 8. The dielectric layer 2 (or the passivation layer 10, if such is provided) is then thinned from the surface opposite to the semiconductor substrate 1, until the further conductor 9 protrudes from the dielectric layer 2 sufficiently far, and an embodiment similar to the one shown in FIG. 1 is thus obtained.

By the described method the semiconductor device can be produced within a standard CMOS process with only few additional method steps, which are furthermore fully compatible with the standard CMOS process. The protruding further conductor 9 facilitates an electrical connection to elements of a further device, especially to elements comprising a gas-sensitive material, like carbon nanotubes, for instance.

Figure 8:
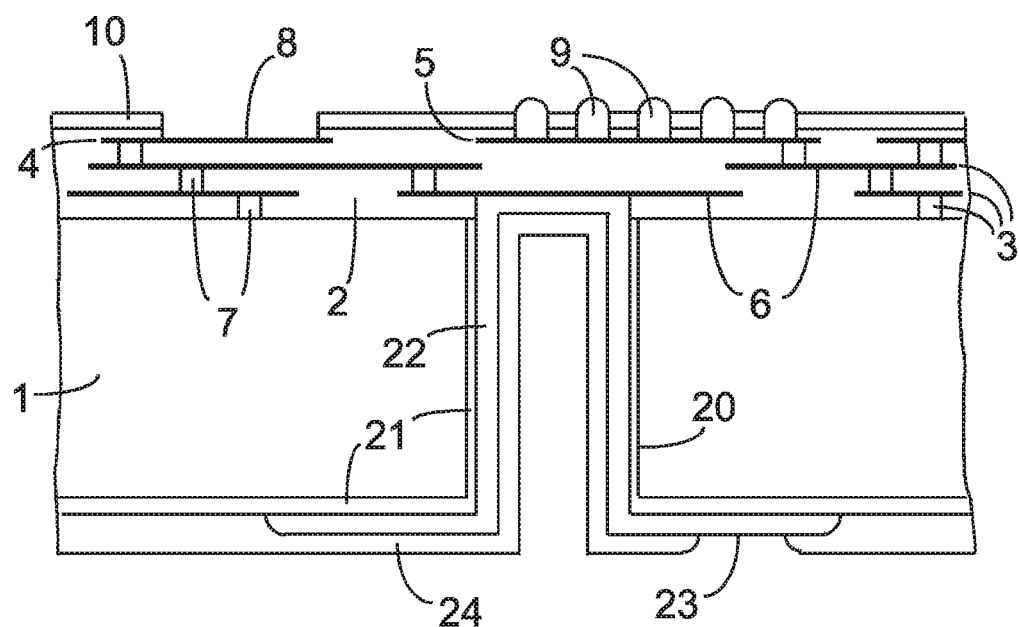
FIG. 8 is a cross section of a further semiconductor device comprising a through-substrate via.

FIG. 8 is a cross section of a further semiconductor device comprising a through-substrate via. A via hole 20 is etched from the rear side into the semiconductor substrate 1, and a rear contact area of one of the conductors 6 of the wiring 3 is uncovered. A further dielectric layer 21 is formed to insulate the semiconductor material. A metallization 22 is arranged in the via hole 20 in contact with the rear contact area of the electrical conductor 6 of the wiring 3. The metallization 22 can be electrically connected with a further rear contact area 23 on a rear portion of the metallization, which is provided for an external electrical connection. Thus an electrical interconnection penetrating the semiconductor substrate 1 is formed. A further passivation layer 24, which is opened above the contact area 23, may be applied on the rear side and on the metallization 22 within the via hole 20.

The invention claimed is:

1. A method of producing a semiconductor device, comprising:
forming a wiring comprising electrical conductors in a dielectric layer on or above a semiconductor substrate;

forming an opening in the dielectric layer to uncover a contact pad formed by one of the conductors;
forming a further opening in the dielectric layer and thus uncovering an area of a further one of the conductors, separate from the contact pad;
filling the further opening with an electrically conductive material; and
thinning the dielectric layer from a side opposite the substrate,
wherein the dielectric layer is thinned without further exposing an uppermost metallization layer,
wherein the electrically conductive material protrudes from the thinned dielectric layer and forms the further conductor,
wherein the height by which the further conductor protrudes ranges from 20 nm to 100 nm.

2. The method of claim 1, wherein
the electrically conductive material is also filled in the opening uncovering the contact pad; and
a portion of the electrically conductive material is removed such that a spacer is formed in the opening by a residual portion of the electrically conductive material and the further opening remains at least half filled.

3. The method of claim 1, wherein the further opening is formed by a trench.

4. The method of claim 1, wherein the further opening is formed by a plurality of parallel trenches.

5. The method of claim 1, wherein the electrically conductive material filling the further opening comprises a metal that is different from the electrical conductors.

* * * * *